(12) United States Patent  (10) Patent No.: US 7,648,504 B2
Heino et al.  (45) Date of Patent: Jan. 19, 2010

(54) BIOABSORBABLE BAND SYSTEM

(75) Inventors: Harri Heino, Tampere (FI); Pertti Törmälä, Tampere (FI); Timo Waris, Helsinki (FI)

(73) Assignee: Bioretec Ltd, Tampere (FI)

( * ) Notice: Subject to any disclaimer, the term of this patent is extended or adjusted under 35 U.S.C. 154(b) by 1225 days.

(21) Appl. No.: 10/657,087

(22) Filed: Sep. 9, 2003

(65) Prior Publication Data

US 2005/0070928 A1  Mar. 31, 2005

(51) Int. Cl.
 *A61B 17/82* (2006.01)
(52) U.S. Cl. ......................................................... 606/74
(58) Field of Classification Search ............ 606/72–75, 606/151, 153–157
See application file for complete search history.

(56) References Cited

U.S. PATENT DOCUMENTS

| 3,111,945 | A | * | 11/1963 | Von Solbrig | 606/74 |
| 3,710,789 | A | * | 1/1973 | Ersek | 606/60 |
| 3,886,630 | A | | 6/1975 | Emery | |
| 4,792,336 | A | * | 12/1988 | Hlavacek et al. | 623/13.18 |
| 4,813,416 | A | | 3/1989 | Pollak et al. | |
| 4,966,600 | A | | 10/1990 | Songer et al. | |
| 5,339,870 | A | | 8/1994 | Green et al. | |
| 5,355,913 | A | | 10/1994 | Green et al. | |
| 5,415,658 | A | * | 5/1995 | Kilpela et al. | 606/69 |
| 5,423,821 | A | * | 6/1995 | Pasque | 606/74 |
| 5,466,262 | A | * | 11/1995 | Saffran | 606/74 |
| D369,960 | S | | 5/1996 | Rohaly et al. | |
| 5,536,270 | A | * | 7/1996 | Songer et al. | 606/74 |
| 5,649,927 | A | | 7/1997 | Kilpela et al. | |
| 5,921,986 | A | * | 7/1999 | Bonutti | 606/60 |
| 6,200,318 | B1 | | 3/2001 | Har-Shai et al. | |
| 7,112,221 | B2 | * | 9/2006 | Harris | 623/13.11 |
| 2002/0120270 | A1 | * | 8/2002 | Trieu et al. | 606/61 |
| 2003/0236555 | A1 | * | 12/2003 | Thornes | 606/232 |

* cited by examiner

*Primary Examiner*—Thomas C Barrett
*Assistant Examiner*—Nicholas Woodall
(74) *Attorney, Agent, or Firm*—Kenyon & Kenyon LLP (57) ABSTRACT

A bioabsorbable band system is provided. The system comprises a bioabsorbable elongated band and two locking member systems. This band system may be used to heal bone fractures or osteotomies.

8 Claims, 13 Drawing Sheets

BIOABSORBABLE BAND SYSTEM

FIELD OF INVENTION

The present invention relates to bioabsorbable band systems for securing bone. Specifically, the present invention relates to bioabsorbable band systems comprising a bioabsorbable band and bioabsorbable locking member systems.

BACKGROUND OF THE INVENTION

Surgical band and locking member systems position cables and locking implants around bones to allow for healing. One common form of a locking implant is a crimp system. These systems are used to crush the cable into engagement with the tissue to retain the cable at a desired position. However, current designs of cable and crimp systems, particularly for surgical use, have significant drawbacks. For example, a tension, which is too low or too high may lead to improper healing or poor medical results.

Also, in many prior art cable and crimp systems there is the possibility for slippage of the cable in the crimp, which can lead to delayed healing. The loosening of the cable, e.g. in bone fracture fixation, can also lead to delayed healing, pain or even to a failure to heal. Also, many prior art crimps cannot be easily locked at a desired tension, and often the desired tension can not be maintained when using a cable loop or winding as there is an inevitable drop in tension when the pliers are removed. Thus, a surgeon typically has to "over shoot" the desired tension, guessing how much of that tension will be lost after the crimping has been completed and the pliers removed, thus significantly increasing the possibility for tensioning errors.

In addition, many prior art crimps are bulky and may cause adverse tensioning in the surrounding tissues, which may result in a negative effect on tissue healing. Another drawback of many prior art cable and crimp systems is that they are made of metal, such as stainless steel. Such extremely stiff materials are mechanically incompatible with bone tissue and therefore, may cause osteolysis below the material, which may lead to implant migration.

Therefore, it is desirable to use less stiff band and locking member systems, thereby preventing osteolysis and implant migration. It may also be desirable to use bands and locking member systems where band slippage in relation to the locking member(s) is not possible. Finally, it may be desirable to use bioabsorbable band and locking member systems, so that the implant will absorb after healing of the bone fracture or osteotomy.

SUMMARY OF THE INVENTION

The present invention provides a bioabsorbable band and locking member system, which may provide accurate tensioning to the band and safe locking of the band around bone.

In an embodiment of the present invention, a bioabsorbable band system for securing a bone fracture is provided, comprising, a bioabsorbable band, a first locking system comprising at least one bioabsorbable fastener, and a second locking system comprising at least one bioabsorbable fastener.

In another embodiment of the present invention, a method to secure a bone fracture or osteotomy with a bioabsorbable band system is provided. The method includes locking the first end of the band to a surface of a bone with the first locking system, passing the second end through side edges of a tissue to be drawn together with the bone, tightening the band, and locking the second end of the band to a surface of the bone.

DETAILED DESCRIPTION

In accordance with the present invention, a bioabsorbable band and locking member system are provided. The system comprises a bioabsorbable elongated band and two locking member systems. The band system of the present invention may be used to heal bone fractures or osteotomies.

Figure 1:
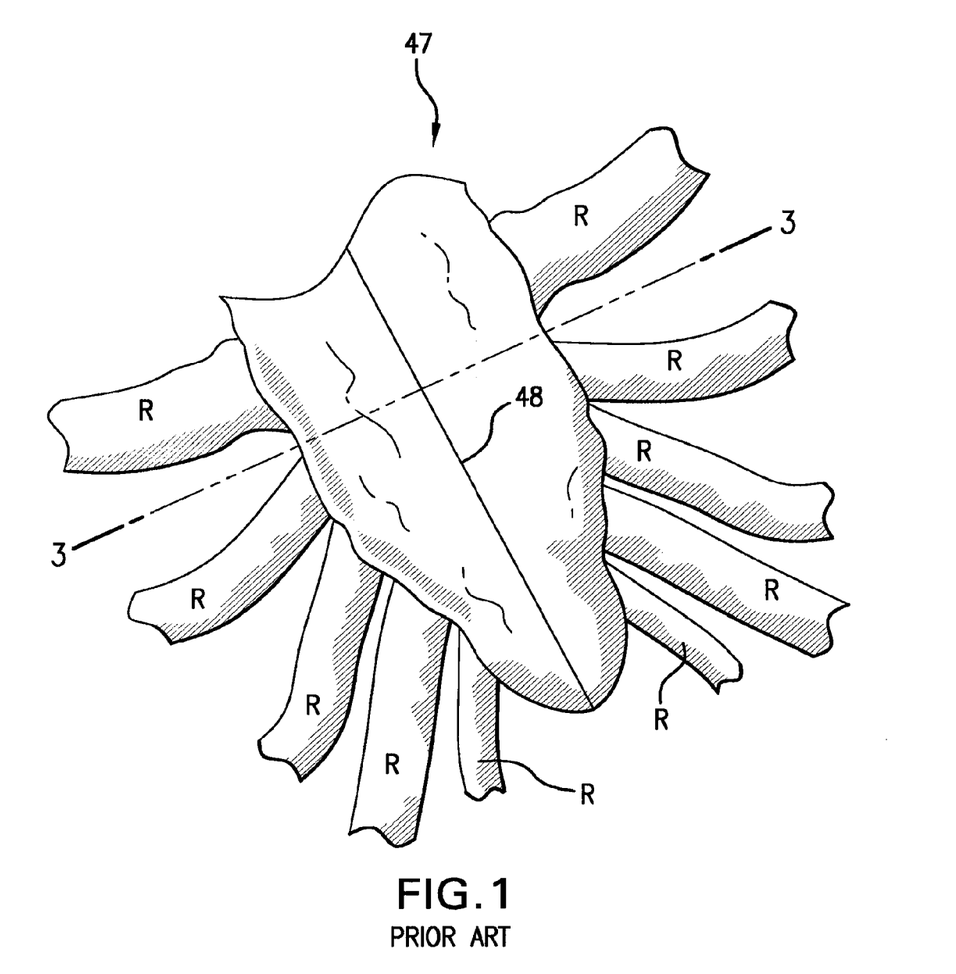
FIG. 1 shows a known sternum in a perspective view with a vertical sternotomy.

FIG. 1 shows an example of part of a sternum 47 with a vertical osteotomy also known as a sternotomy 48 and the ends of several ribs R fixed to the sternum. Also shown is a cross-section line 3-3. The band system of the present invention may be used to heal sternotomys.

The bioabsorbable band may comprise a flat elongated body having a lower side and an upper side. The band may be fabricated from bioabsorbable fibers through textile technology such as forming fabric through braiding or weaving, or molded from bioabsorbable polymer, copolymer or polymer blend through polymer technology, such as injection molding or extrusion.

The locking member systems may include a first bioabsorbable locking member system for securing one end of the band on or around a bone, and a second bioabsorbable locking member system for securing the other end of the band on or around the bone, and/or on the first locking member. The locking member systems may be solid, stiff objects, like pins, rods, screws, bolts, rivets or tacks, which penetrate the band to lock it in relation to the bone. Such locking systems are known in the art, as for example described U.S. Pat. No. 6,221,075 (screws), U.S. patent application Ser. No. 09/410,288 (tacks) and in FR Pat. No. 2,741,255 (bolts or rivets), all hereby incorporated by reference.

FIGS. 2A-2I show embodiments of a bioabsorbable band, which may be used with the band system of the present invention. The bands shown in FIGS. 2A-2I may be concave in order to achieve sufficient contact between the band and a convex bone surface. In addition, the side of the band that is in contact with the bone may have projections, such as ridges, pyramids or other protuberances, in order to reduce the area of contact with the bone, thus reducing the risk of bone necrosis.

The various bioabsorbable materials available to manufacture the band of the present invention may include woven, braided, knitted, bioabsorbable fibers, solid bioabsorbable plates, molded bioabsorbable polymers, copolymers, or polymer blends, and bioabsorbable meshes. Depending on the desired properties, any of the above material structures may be used individually or in combination. For example, the various material structures each have a combination of unique properties, such as flexibility, stiffness, strength, toughness, and elasticity.

Figure 2A:
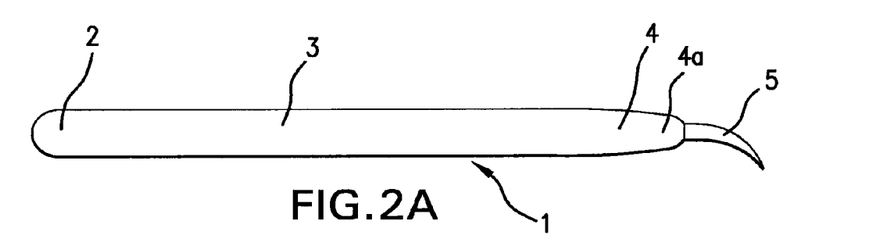
FIGS. 2A-2I show embodiments of the band of the present invention.

As shown in FIG. 2A, a bioabsorbable elongated band 1 of the present invention may have a first end 2, a second end 4, and a longitudinal, flexible body 3. Second end 4 may have a tapered surface 4a and include a needle 5. The flexible body 3 in this embodiment may be molded from a bioabsorbable polymer component.

Figure 2B:
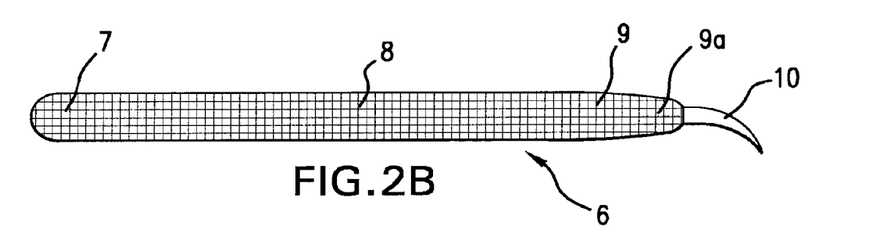

FIG. 2B shows another embodiment of a band of the present invention in which the band 6 has been manufactured of bioabsorbable fibers through textile technology, such as knitting, weaving, braiding or some combination thereof. In this embodiment, the fibrous band 6 includes a first end 7, a longitudinal, flexible body 8, and a second end 9, which has a tapered end 9a. Here again, the band 6 may include a needle 10 affixed to the tapered end 9a.

Figure 2C:
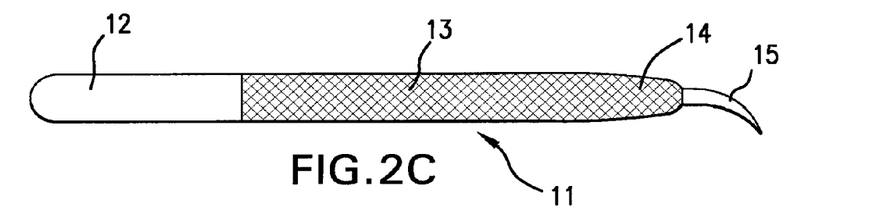

Band 11 of FIG. 2C includes a first end 12, comprising a stiff, strong and tough plate, which is combined with a flexible, fibrous body 13, and a second end 14, to which a needle 15 may be affixed.

Figure 2D:
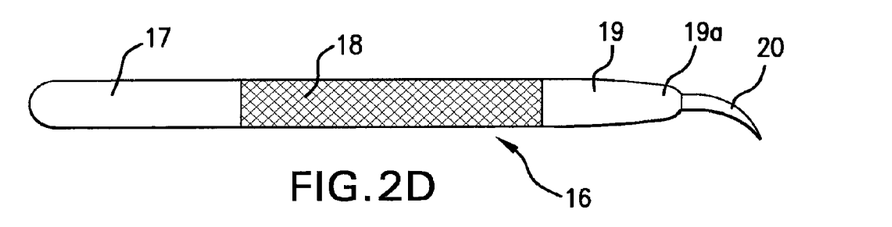

In FIG. 2D an embodiment of the band 16 of the present invention is shown including a first end 17, comprising a stiff, strong and tough plate, combined with a flexible, fibrous body 18, and a second end 19 also comprising a plate. The second end 19 may be a tapered end 19a and have a needle 20 attached thereto.

Figure 2E:
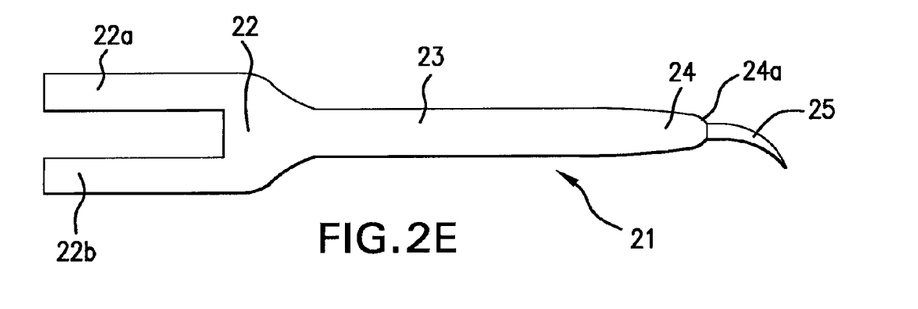

FIG. 2E shows another embodiment of the band of the present invention. In this embodiment, the band 21 includes a first forked end 22, including a first leg 22a and a second leg 22b. The body 23 of the band 21, may be a flexible body as described in FIG. 2A or a plate as described in FIG. 2C. The second end 24 may again have a tapered end 24a and a needle 25 attached thereto.

Figure 2F:
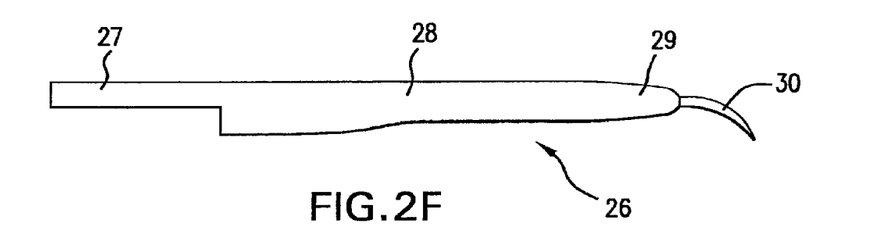

Another embodiment of the present invention is shown in FIG. 2F. In this embodiment, a portion of the first end 27 of the band 26 is narrowed as compared to the body 28 and the second end 29. End 29 may be tapered and a needle 30 may be affixed thereto.

Figure 2G:
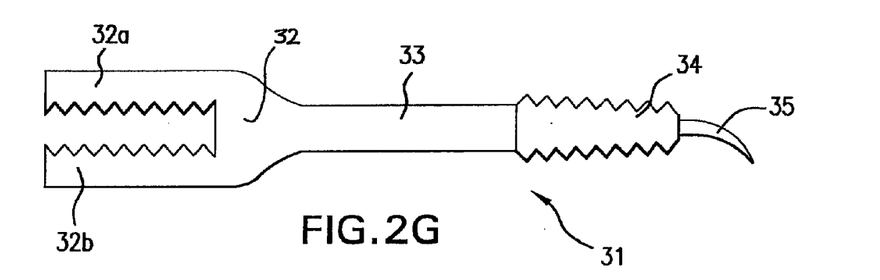

FIG. 2G shows yet another embodiment of the band of the present invention. Band 31 comprises a first end 32 including a corrugated notch with two legs 32a and 32b. Band 31 also includes a stem or body 33 and a corrugated second end 34 to which a needle 35 may be attached.

Figure 2H:
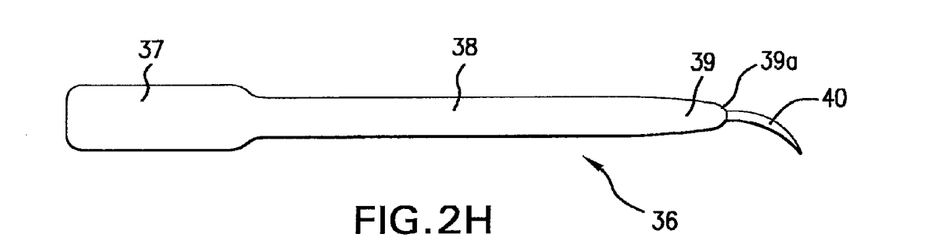

FIG. 2H shows a band 36 comprising a first end 37, which may be a stiff and strong plate, a flexible body 38, and a second end 39, which may be a tapered end 39a and include a needle 40 attached thereto. In this embodiment, the first end 37 may be wider than the rest of the band 36.

Figure 2I:
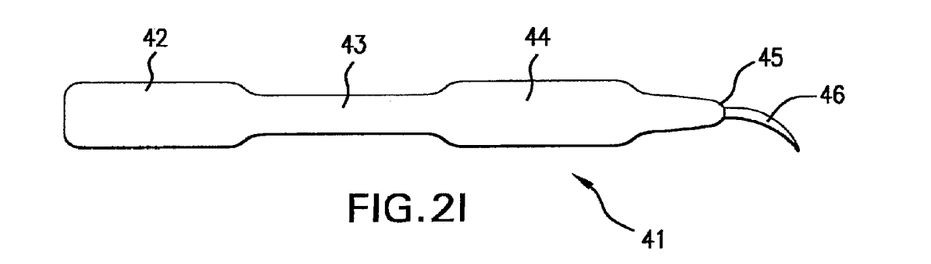

FIG. 2I shows another embodiment of the band of the present invention. In this embodiment, the band 41 includes both first end 42 and second end 44, which may be stiff plates. In contrast, the body 43 may be flexible. Second end 44 has a tapered end 45 with a needle 46 attached thereto.

In another embodiment of the present invention, a method of using a band system of the present invention is provided. Generally, to use the band system of the present invention, the first end of the band may be locked to a bone surface using at least one fastener. The second end of the band, including a needle, may be passed through the side edges of the tissue to be drawn together (for example, around the operated sternum for closing of a sternotomy). The second end of the band, which is bent around the bone particles to be fixed together, may be tightened over the osteotomy. The proper tension may be maintained on the band by drawing the second end of the band. This tensioning or drawing may be performed by hand or using a specific tensioning measurement device. One such device is described in U.S. Pat. No. 6,200,318, which is hereby incorporated by reference. In either instance, maintaining a controlled pressure is important in order to allow for proper healing of the osteotomy.

Thereafter, the second end of the band is fixed under proper tension on bone and/or on the surface of the first end of the band by forming a suitable hole through the second end of the band, optionally through the first end of the band, and into the bone below the band.

FIGS. 3A-3J show an example of a method for using an embodiment of the band system of the present invention.

Figure 3A:
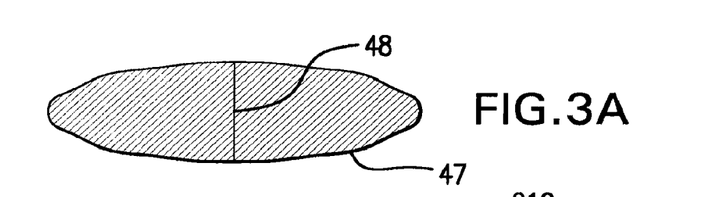
FIGS. 3A-3J show a method of closing the vertical sternotomy of FIG. 1 with an embodiment of the band system of the present invention as seen along plane 3-3 of FIG. 1.
Figure 3B:
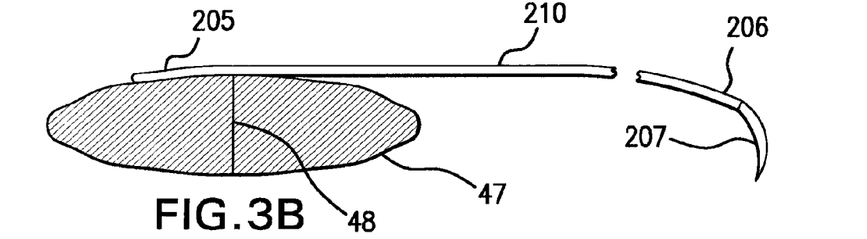

FIG. 3A shows a cross-section of sternum 47 along plane 3-3 of FIG. 1. In FIG. 3B an embodiment of a band 210 of the present invention begins to be wrapped around the sternum 47 and specifically across the sternotomy 48. First end 205 may be fixed to the sternum 47 temporarily with a device, like a clamp or by hand (not shown).

Figure 3C:
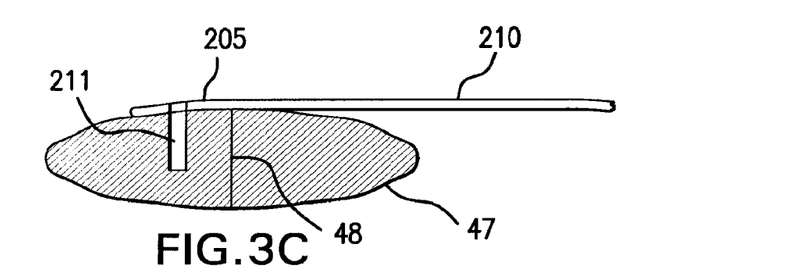
Figure 3D:
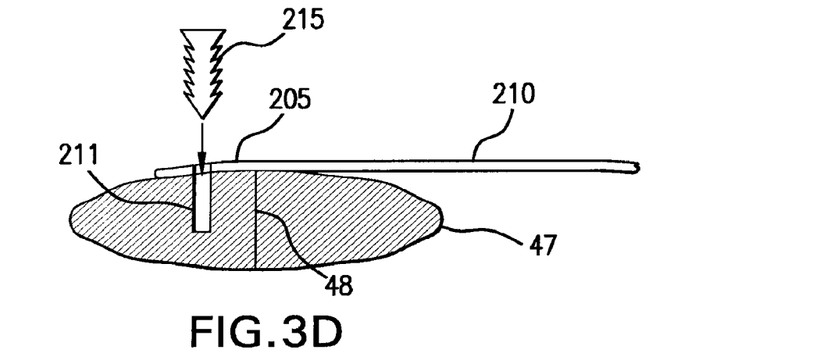
Figure 3E:
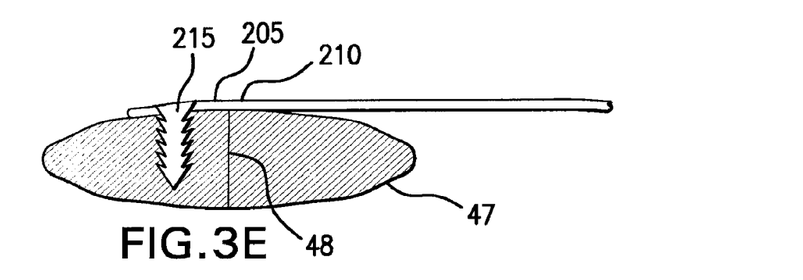
Figure 3F:
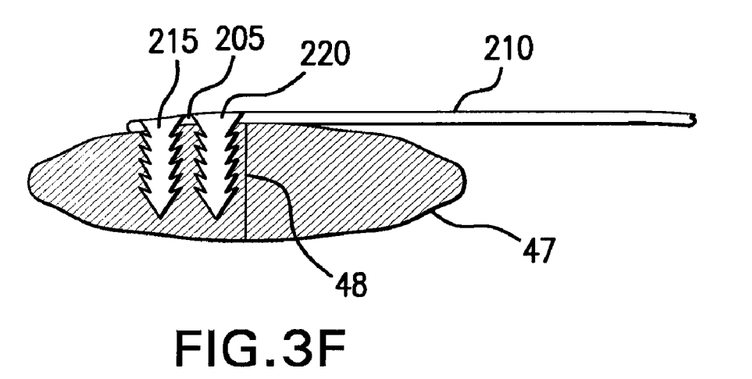
Figure 3G:
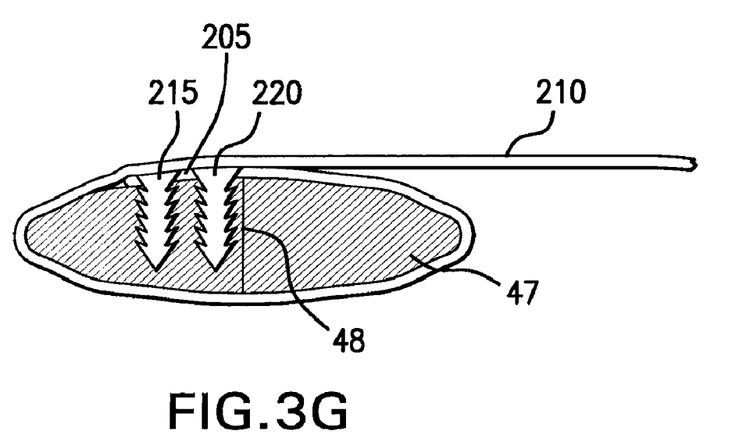

Next a hole 211 may be drilled through the first end 205 of the band 210 into the sternum 47. The fastener 215 may be tapped in or a counter sink may be used to fasten the fastener 215 in the bone 47, as shown in FIGS. 3C to 3E. A second fastener 220 may also be used to attach or fix first end 205 to the sternum 47, as shown in FIG. 3F. Fasteners 215 and 220 comprise the first locking system, however, any number of fasteners in any desired configuration may be used by the surgeon.

As shown in FIGS. 3B to 3G, after securing the first end 205 of the band 210 firmly to the surface of the sternum 47, the second end 206 of the band, including a needle 207 may be passed through the tissues around the sternum (not shown) and tightened over the first end 205 of the band 210.

Figures 3H, 3I:
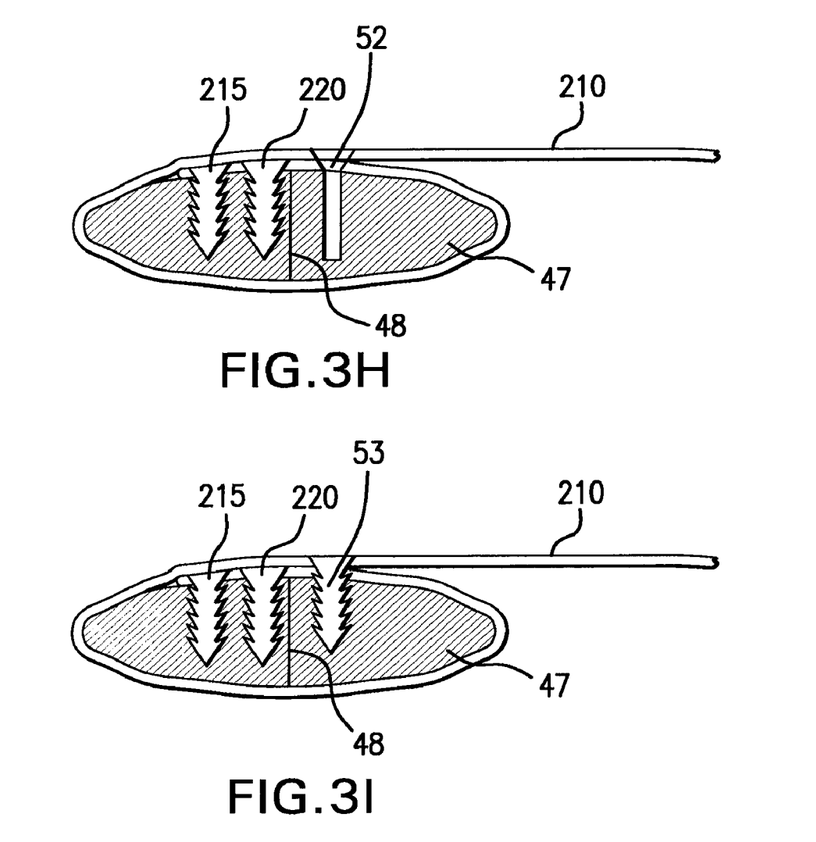
Figure 3J:
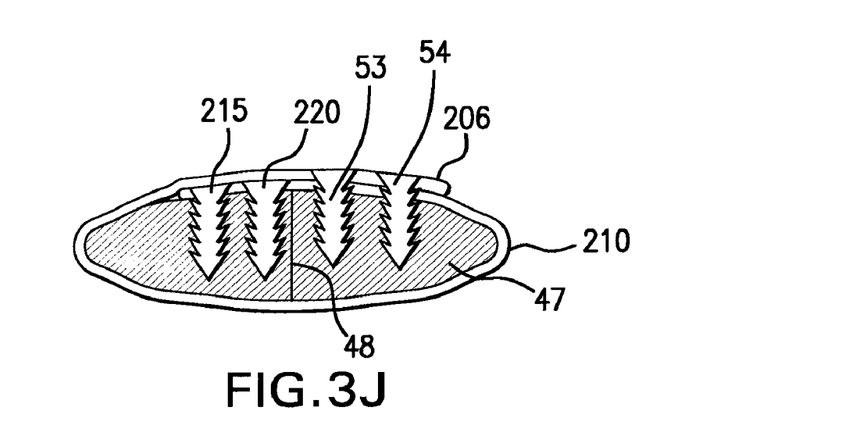

FIGS. 3H to 3J show the last steps of the method. To secure the second end 206, another drill hole 52 may be drilled through the second end 206, band 210, and the sternum 47. Fastener 53 may be tapped in or a counter sink may be used to fasten the fastener 53 in the bone 47. Similar to the first end 205, a second fastener 54 may be used in addition to fastener 53, thus forming the second locking system. After securing the second end 206 of band 210, band 210 may be cut thus resulting in a firm closure of the sternotomy 48.

The advantages to using this system include the controlled, continuous tightening of a band for optimal tensioning without the restriction of initial fixation elements or holes, lack of slippage between the band and the bone and the locking systems, and the lack of crimps, which may cause adverse effects, like pain or oedema.

The oriented and/or reinforced materials of the implants of this invention typically have initial tensile strengths of about 100-1000 MPa, bending strengths of about 100-500 MPa and shear strengths of about 80-300 MPa. Additionally, they can be made stiff, tough, and/or flexible. These mechanical properties are superior to those of non-reinforced absorbable polymers which typically show strengths between 40 and 100 MPa and may additionally be brittle.

Another advantage of the present invention is that it does not require bulky crimps. The elements of the band system may be made relatively thin e.g. with band thicknesses about 0.5-2 mm (with widths about 3-15 mm) and locking member diameters about 0.5-5 mm and lengths about 4-20 mm.

FIGS. 4A to 4G show the same type of injury as seen in FIG. 1, but with various embodiments of the band system of the present invention applied thereto. In all of these embodiments, the band is wrapped around the sternum and the sternotomy and then attached/locked to the sternum.

Figure 4A:
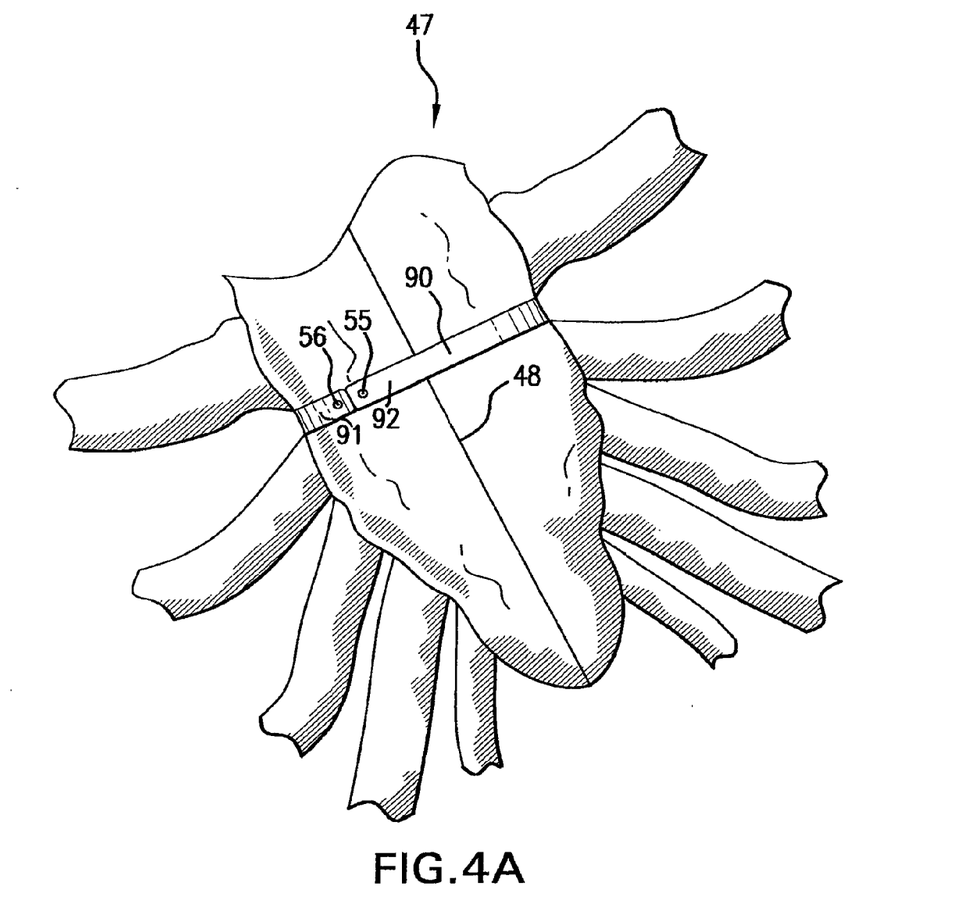
FIGS. 4A-4G show various embodiments of band systems of the present invention in use.

FIG. 4A shows a band 90 with a first end 91 and a second end 92. The band 90 has been wound around the sternum 47 and locked into place on the surface of the sternum 47 with a first locking member 56 attaching first end 91 of the band 90 to the sternum 47 and a second locking member 55 attaching the second end 92 of the band 90 to the sternum 47. The locking members 55 and 56 shown, may be any type of bioabsorbable fastener, such as pins, screws, tacks, or combinations thereof and the number of locking members is not intended to be limiting. For example, one or more fasteners may be used to attach either end of the band to bone and no specific layout or configuration for the fasteners is required. One of ordinary skill in the art will understand that a doctor performing this type of procedure should be able to determine the optimal level of attachment needed to secure the band to or around the injury.

Figure 4B:
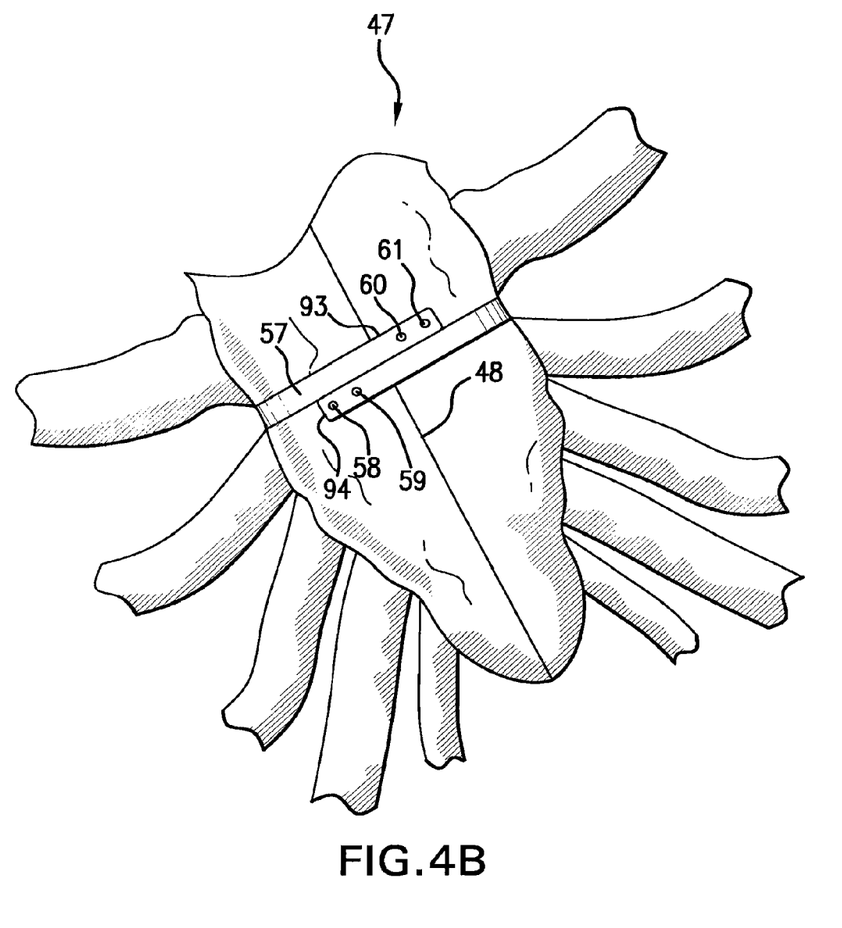

FIG. 4B shows another embodiment of the band system of the present invention. In FIG. 4B, band 57 having first end 93 and second end 94 is wrapped around and attached to the sternum 47. A first locking system including fasteners 60 and 61 is used to attach the first end 93 of band 57 to the sternum 47. In addition, a second locking system including fasteners 58 and 59 is used to attach second end 94 of the band 57 to the sternum 47. In this embodiment, the first and second ends 93 and 94 of band 57 are side by side on opposite sides of the sternotomy 48.

Figure 4C:
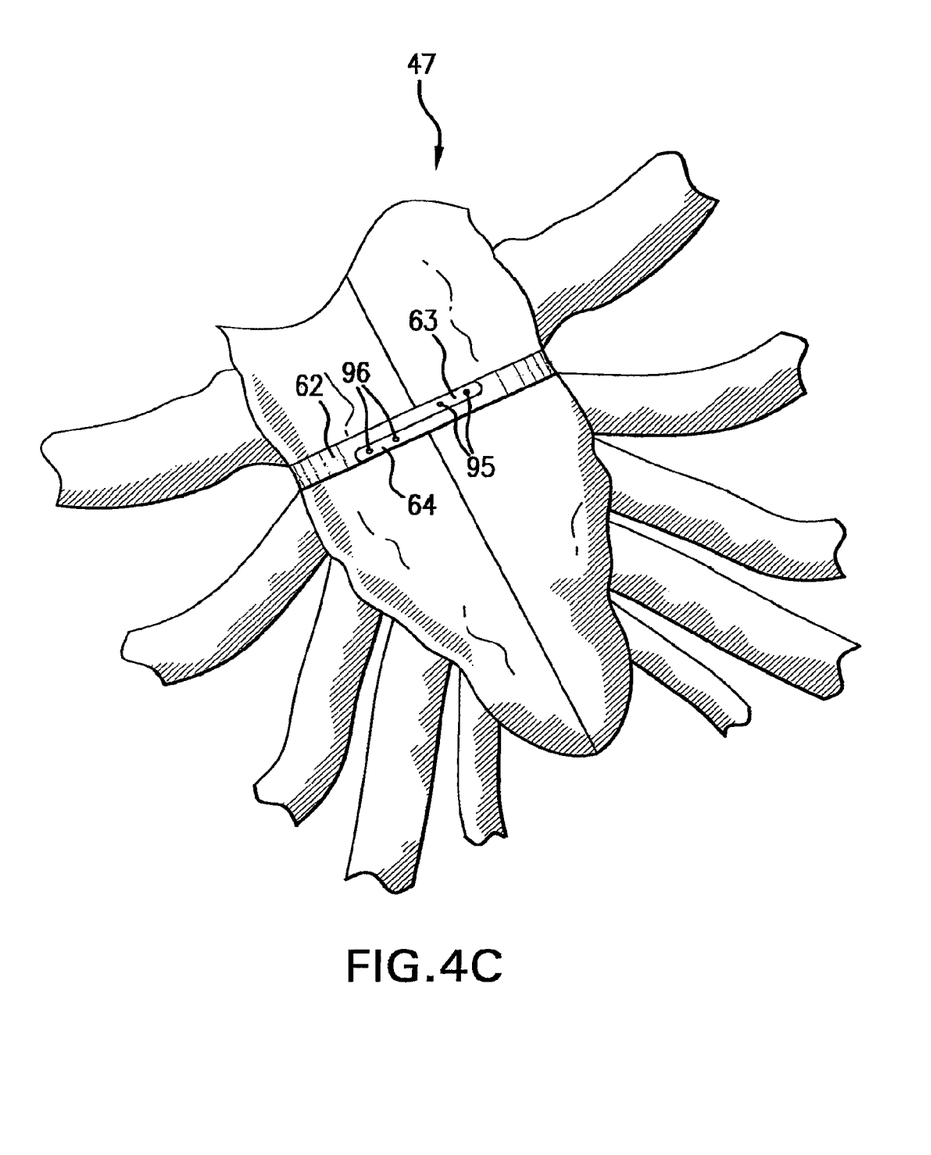

In FIG. 4C, an embodiment of the present invention is shown including a band 62 having first and second ends 63 and 64 that are narrower than the body of the band. The first and second ends 63 and 64 are narrowed in order to reduce the contact area between the band 62 and the sternum 47. In this embodiment, the first locking system 95 and the second locking system 96 each comprise two fasteners.

Figure 4D:
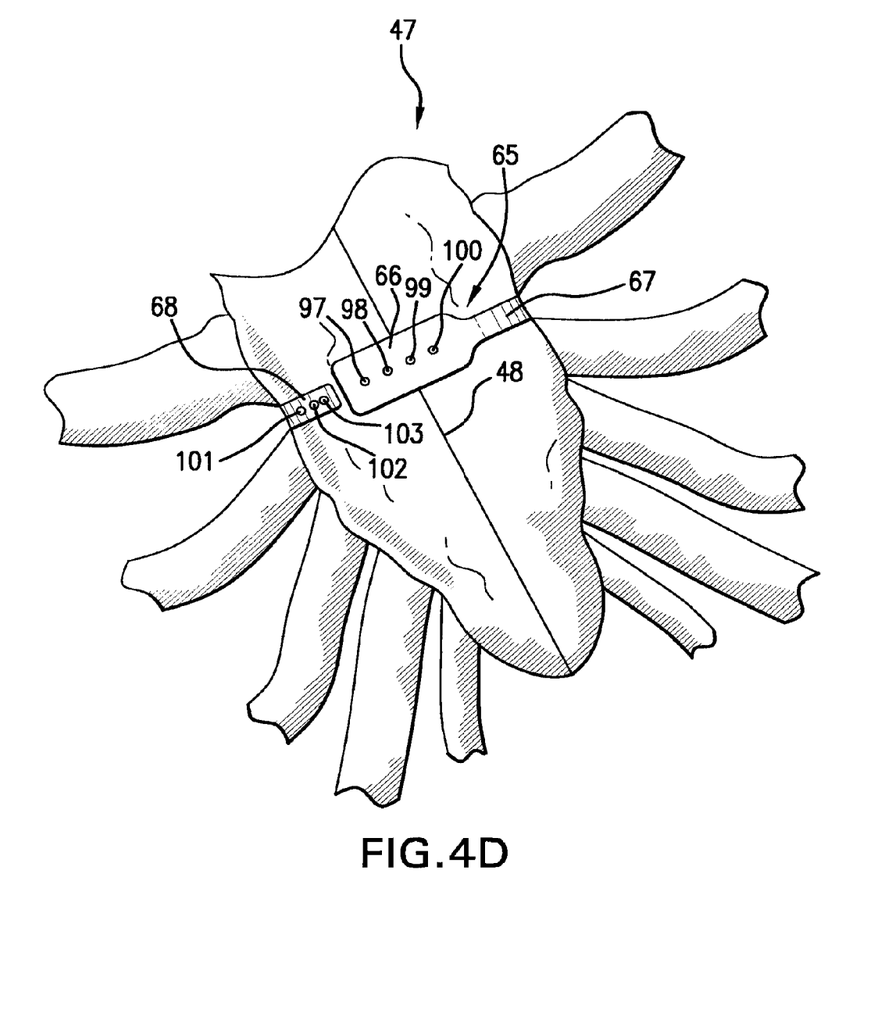

FIG. 4D shows another embodiment of the present invention. Band 65 includes a flexible body 67 having high tensile strength, a first end 68, and second plate end 66. As is shown, second end 66 covers the sternotomy 48 and is attached to the sternum 47 with four fasteners 97 to 100, two on each side of the sternotomy 48, thus forming the first locking system. The second end 68 is attached to the sternum 47 with three fasteners 101 to 103, thus forming the second locking system.

The embodiment shown in FIG. 4D is advantageous because the stiff and strong plate of second end 66 keeps the sternotomy effectively closed against a number of different forces, which may try to separate the sternum parts from each other. For example, tensile forces, shear forces, and bending forces, may all be exerted against the sternum parts at various times. The band system of the present invention, and particularly the embodiment shown in FIG. 4D, prevents the sternum from pulling apart, sliding, and bending, as a result of these forces. In this way the negative effects of physiological forces, which may open the sternotomy and delay or prevent healing, are eliminated.

Figure 4E:
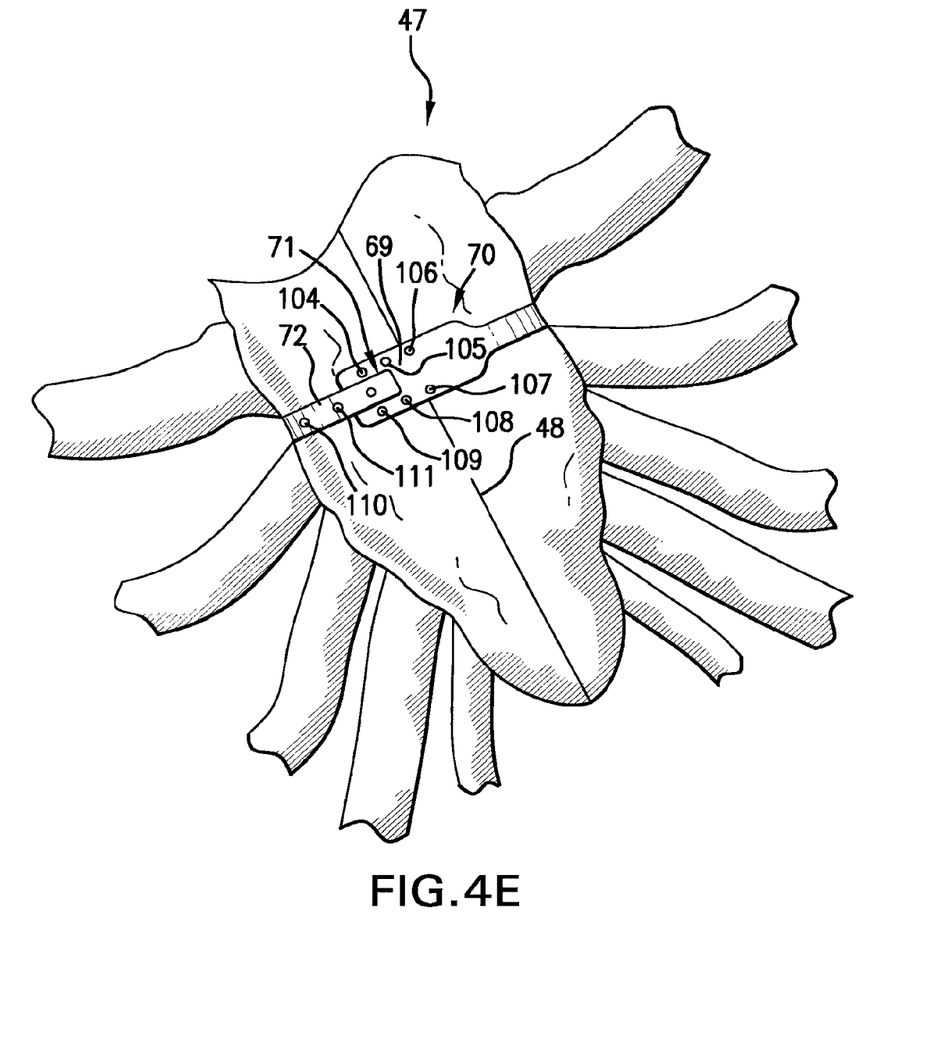

The band system shown in FIG. 4E is similar to the one shown in FIG. 4D, however, band 70 has a first end 72, which fits into a notch 71 in second end 69. First end 72 may be attached to sternum 47 using a first locking system including fasteners 110 and 111. In addition, as in FIG. 4D, fasteners 104 to 109, which comprise the second locking system, attach second end 69 to both sides of sternotomy 48.

Figure 4F:
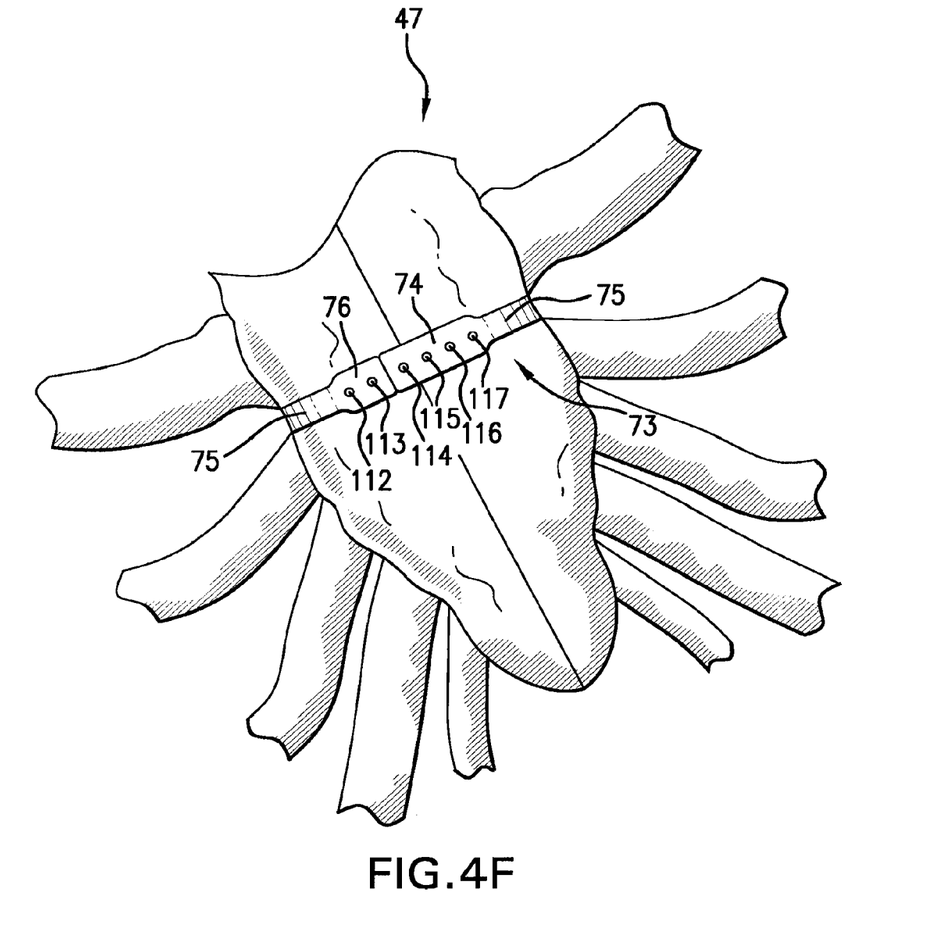

The embodiment of the present invention shown in FIG. 4F is also similar to that shown in FIG. 4D. However, band 73 has a flexible body 75 and two plate ends, first end 76 and second end 74. The first end 76 may be fixed to the sternum 47 with a first locking system including fasteners 112 and 113. The second end 74 crosses the sternotomy and may be fixed to the sternum 47 with a second locking system including four fasteners 114 to 117. Here again, the second locking system may be configured so that there are two fasteners on each side of the sternotomy.

Figure 4G:
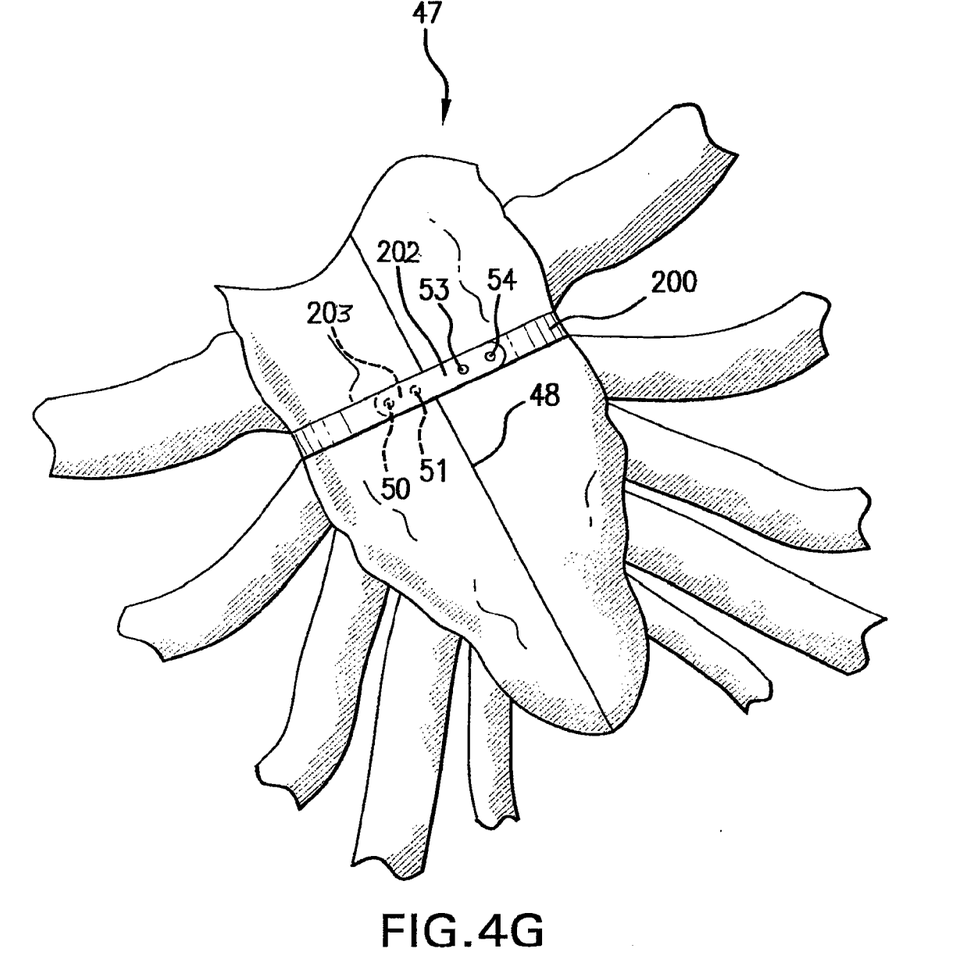

FIG. 4G shows an embodiment of the invention in which the first end 202 of band 200 overlaps second end 203 and the ends 202 and 203 overlap the sternotomy 48. The fixation may include a first locking system including fasteners 53 and 54, and a second locking system including fasteners 50 and 51.

The bioabsorbable band systems of this invention may be manufactured of bioabsorbable polymers, copolymers or polymer mixtures or alloys by molding, sintering and/or with solid state deformation methods such as those described in U.S. Pat. No. 4,743,257, U.S. Pat. No. 4,968,317, EPO Pat. No. 0423155, AU Pat. No. 729801, EPO Pat. No. 1009448 and in U.S. Pat. No. 6,406,598, all of which are hereby incorporated by reference.

Strong and tough oriented and/or self-reinforced structures are especially advantageous for the systems of this invention. They may be created during extrusion or injection molding of absorbable polymeric melt through a suitable die or into a suitable mold at high speed and pressure. When cooling occurs at suitable conditions, the flow orientation of the melt remains in the solid material as an oriented and/or self-reinforced structure. In an advantageous embodiment, the mold may have the form of an element of the system, including a band or a locking member, but it is also possible to manufacture the implants of the invention by machining (possibly using also heat) and by thermoforming of injection-molded or extruded semi-finished products.

It is advantageous to make the implants of melt-molded, solid state drawn or compressed, bioabsorbable polymeric materials, as described in U.S. Pat. No. 4,968,317 or U.S. Pat. No. 4,898,186, both of which are hereby incorporated by reference.

The reinforcing fibers of the implants may also be ceramic fibers, such as bioabsorbable hydroxyapatite, bioactive glass, or tricalcium phosphate fibers. Such bioabsorbable, ceramic fiber reinforced materials are described in European Patent Application No. 0146398 and in WO 96/21628, both of which are hereby incorporated by reference.

The oriented and/or self-reinforced or otherwise fiber reinforced implants of this invention may be manufactured by molding the reinforcement fiber-polymer matrix to the final product in a mold, whose mold cavity has the form of the final product (e.g. a band or a locking member) or the final form may be machined mechanically (possibly also using heat) on a preform, such as a melt-molded and solid-state drawn rod, as described in U.S. Pat. No. 4,968,317, which is hereby incorporated by reference.

The reinforcement elements may extend into any protrusions or ridges of various elements of the system. The reinforcement elements may also turn spirally around the long axis of the various elements of the system. Also other different orientations of reinforcement elements in elongated samples which are familiar from composite technology may be applied to the present invention. However, a general feature of orientation and/or fiber-reinforcement or self-reinforcement in the present invention is that many of the reinforcing elements are oriented in such a way that they can carry effectively the different external loads (such as tensile, bending and shear loads) that are directed to the healing bone fracture or osteotomy.

According to an advantageous embodiment of the invention, elements of the system, such as a band and/or a locking member, may have a special coating layer on their surfaces and may contain one or more bioactive substances, such as antibiotics, chemotherapeutic substances, growth factors like bone morphogenic proteins, substances accelerating the healing of the wound and osteotomy, hormones or other drugs and the like. Such bioactive elements are especially advantageous in surgical use, because they contribute biochemically to the healing of the lesion in addition to providing mechanical support.

The implants of the present invention may be sterilized by well known sterilization techniques, depending on the type of material used in manufacture of the implant. Suitable sterilization techniques include radiation sterilization such as cobalt 60 irradiation or electron beams, ethylene oxide sterilization, and the like.

After the description above of the present invention and certain specific embodiments thereof, it will be readily apparent to those skilled in the art that many variations and modifications may be made to the present invention without departing from the spirit and scope thereof.

We claim:

1. A method to secure two sections of bone in a transverse bone fracture or an osteotomy with a bioabsorbable band system, comprising:
   providing a bioabsorbable band system, comprising:
      a bioabsorbable band having a first end and a second end;
      a first locking system comprising at least one bioabsorbable fastener; and
      a second locking system comprising at least one bioabsorbable fastener;
   locking the first end of the band to a first surface of a bone with the first locking system;
   then wrapping the second end of the band around the bone;
   then stretching the band to secure the two sections of the bone in the transverse bone fracture or the osteotomy together; and
   then locking the second end of the band to a second surface of the bone.

2. The method of claim 1, wherein locking the first end of the band further comprises drilling at least one hole through the first end of the band into the first surface of the bone, and inserting a fastener in said hole.

3. The method of claim 1, wherein locking the second end of the band further comprises drilling at least one hole through the second end of the band and into the second surface of the bone, and inserting a fastener in said hole.

4. The method of claim 3, wherein drilling further comprises drilling the hole through the first end of the band.

5. The method of claim 1, wherein wrapping further comprises inserting a needle attached to the second end of the band through a tissue to be drawn together with the bone.

6. The method of claim 1, wherein the first end and the second end overlap.

7. The method of claim 1, wherein the band encircles the two sections of the bone fracture or the osteotomy.

8. The method of claim 1, wherein the band is elastic.

* * * * *

UNITED STATES PATENT AND TRADEMARK OFFICE
CERTIFICATE OF CORRECTION

PATENT NO. : 7,648,504 B2  Page 1 of 1
APPLICATION NO. : 10/657087
DATED : January 19, 2010
INVENTOR(S) : Heino et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1547 days.

Signed and Sealed this

Twenty-third Day of November, 2010

David J. Kappos
*Director of the United States Patent and Trademark Office*